US00PP37557P2

(12) United States Plant Patent
Korlipara

(10) Patent No.: US PP37,557 P2
(45) Date of Patent: Aug. 4, 2026

(54) ***AGASTACHE* PLANT NAMED 'Peach Pearl'**

(50) Latin Name: ***Agastache cana* x *cusickii***
Varietal Denomination: Peach Pearl

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/429,858

(22) Filed: Dec. 22, 2025

(51) Int. Cl.
*A01H 5/02* (2018.01)
*A01H 6/50* (2018.01)

(52) U.S. Cl.
USPC ..... Plt./399

(58) Field of Classification Search
USPC ..... Plt./263.1, 399
See application file for complete search history.

(56) References Cited

U.S. PATENT DOCUMENTS

PP25,886 P3 * 9/2015 Hansen ..... A01H 5/02
Plt./360

* cited by examiner

*Primary Examiner* — Karen M Redden
(74) *Attorney, Agent, or Firm* — Klarquist Sparkman, LLP

(57) ABSTRACT

A new and distinct *Agastache* cultivar named 'Peach Pearl' distinguished by its high number of flowers per branched flowering stem, peachy-orange colored flowers, floret size, and large mounding habit.

2 Drawing Sheets

Latin name of the genus and species of the plant claimed: *Agastache cana* x *cusickii.*

Variety denomination: 'Peach Pearl'.

BACKGROUND

The present application relates to a new and distinct variety of *Agastache* named 'Peach Pearl'. *Agastache* is in the family Lamiaceae. *Agastache* 'Peach Pearl' originated as a part of a planned breeding program to produce large, flowered plants with high crown counts. The resulting plant was selected when growing in a cultivated area in Canby, Oregon.

SUMMARY

'Peach Pearl' is distinguished from other known *Agastache* varieties due to the following unique combination of characteristics:

1. High number of flowers per branched flowering stem
2. Peachy-orange color
3. Individual floret size of up to 32 mm long and 9 mm wide
4. A large, mounding habit with an excellent crown count The parents of this variety are 'AGA2293' (seed donor; unpatented) and 'AGA2219' (pollen donor; unpatented). Both parents are proprietary breeding stock. They are not publicly available and are only known by the provided serial number.

The new variety is distinct from other known *Agastache* varieties, for example, as compared to 'Pink Pearl' (U.S. Plant Pat. No. 36,637), which has pink flowers and grows to 45.0 cm wide and 42.0 cm tall, 'Peach Pearl' has bright to pale peachy-orange flowers and a larger habit of up to 56 cm high by 67 cm wide. As compared to *Agastache* 'Kudos Mandarin' (U.S. Plant Pat. No. 25,381), which is 35 cm wide and 38 cm tall to the top of the flowers, *Agastache* 'Peach Pearl' has a larger habit.

The new cultivar has been reproduced only by asexual propagation by tip cuttings and tissue culture. Each of the progeny exhibit identical characteristics to the original plant. Asexual propagation by tip cuttings and tissue culture was performed using standard micropropagation techniques in Canby, Oregon, and shows that the characteristics described herein come true to form, are firmly fixed, and are established and transmitted through succeeding propagations.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to *The Royal Horticultural Society Colour Chart,* $5^{th}$ edition, 2007.

BRIEF DESCRIPTION OF THE DRAWING(S)

Figure 1:
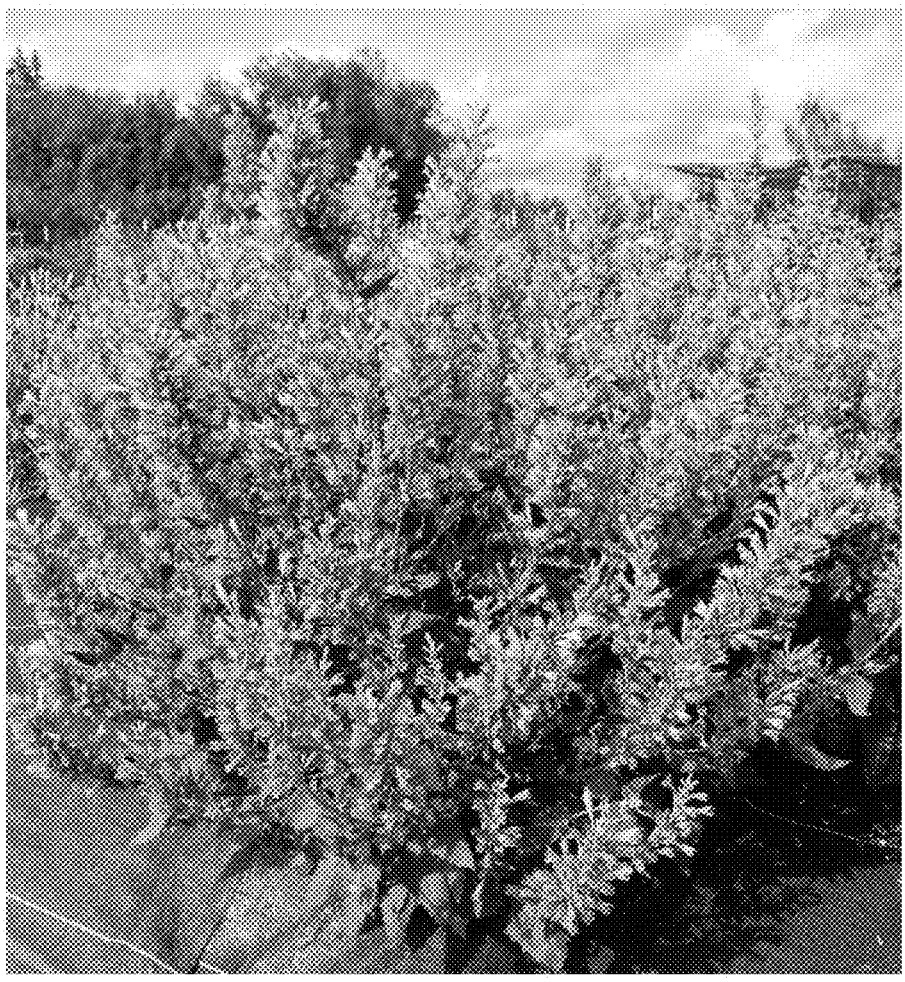
FIG. 1 shows a 7-month-old plant, field grown in full sun in Canby, Oregon. The photograph was taken in July 2024.
Figure 2:
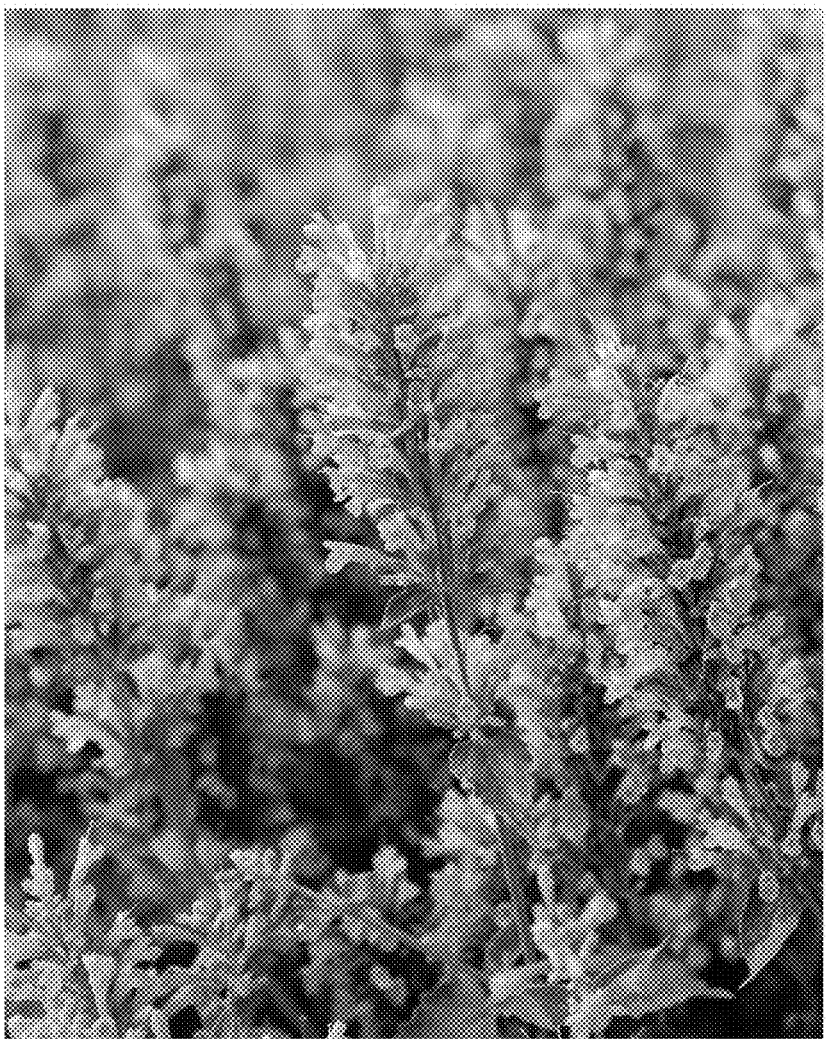
FIG. 2 shows a close-up of flowers of an 8-month-old plant, field grown in full sun in Canby, Oregon. The photograph was taken in August 2024

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

The following is a detailed description of the new *Agastache* cultivar based on observations taken in June of an eighteen-month-old plant, field grown in full sun in Canby, Oregon. Canby is Zone 8 on the USDA Hardiness map. Temperatures range from a high of 95° F. in August to an average of 32° F. in January. Normal rainfall in Canby is 42.8 inches per year.

Parentage:

*Female parent*.—'AGA2293'.

*Male parent*.—'AGA2219'.

Plant:

*Type*.—Herbaceous perennial.

*Growth habit*.—Upright.

*Vigor*.—Very high.

*Plant height*.—56 cm high at top of inflorescence.

*Plant spread*.—67 cm wide.

*Number of crowns*.—41 main stems from the base that branch at every node.

*Hardiness*.—USDA Zones 6-10.

Leaves:

*Type*.—Simple.

*Shape*.—Ovate.

*Arrangement*.—Opposite.

*Size*.—Length: Up to 38 mm. Width: Up to 28 mm.

*Color*.—Leaf: Upper Surface: RHS 138D including venation. Lower Surface: Closest to RHS 138B with venation RHS 138D.

*Venation pattern*.—Pinnate.

*Fragrance*.—Aromatic.

*Margin*.—Crenate.

*Apex shape*.—Acute.

*Base shape*.—Truncate.

*Surface texture*.—Pubescent.

*Petiole description*.—Color: RHS N138D. Length: 7-8 mm. Width: 2 mm. Texture: Pubescent.

Inflorescence:

*Quantity of inflorescences*.—Approximately 41 per plant.

*Flowers per inflorescence*.—Approximately 425-475 per central flowering stem.

*Bud*.—Length: 24 mm. Width: 5.5 mm at widest point prior to opening. Shape: Tubular. Texture: Pubescent. Color: RHS 33C, developing from RHS 34C to RHS 33C.

*Flower*.—Type: Zygomorphic. Shape: Tubular, bilabiate. Floret Size: Up to 32 mm long and 9 mm wide. Inflorescence Type: Terminal spike with up to 15 whorls. Flower Number per Inflorescence: About 400-450 per entire stem and 80-200 per branch. Inflorescence Size: Up to 25 cm long and 6 cm wide. Bloom Period: June through frost in Canby, OR. Lastingness: Spikes last about 4 weeks on the plant, individual flowers last about 7-10 days. Fragrance: Aromatic. Peduncle Length: Up to 5 cm. Peduncle Width: Up to 3 mm. Texture: Pubescent. Color: RHS 138B. Pedicel: Length 3 mm, texture pubescent, color RHS 145B.

*Corolla*.—Length: 32 mm. Width: 7 mm. Corolla Description: Tube measures 26 mm long and from 1.5 to 9 mm wide, flaring into 5 lobes. Surface: The inner and outer surfaces are RHS 33C. Color fades to RHS 19B. The inner surface is glabrous and the outer surface is pubescent. Lobe Descriptions: The two top joined lobes are oblong in shape, have obtuse tips and entire margins measuring 4.5 mm wide and 4.5 mm long. Two of the three lower lobes spread sideways and are reflexed, have acute tips, and entire margins measuring 3 mm long and 4 mm wide. The final lower lobe is cupped, broadly ovate, notched at the tip, and has a serrate margin, measuring 6 mm wide and 4 mm deep.

*Calyx*.—Shape: Campanulate. Arrangement: 5 lobes that are ovate in shape and measure 2 mm long. Size: 8 mm long and 2 mm wide. Apex: Acuminate. Margins: Entire. Texture: Pubescent outer surface and glabrous inner surface. Color: Outer surface closest to RHS 145A and inner surface RHS 145B.

*Pistil*.—1, 33 mm long.

*Ovary*.—1 mm long, colored RHS 144A.

*Style*.—32 mm long, RHS NN155G at bottom blending to RHS 66A at the top.

*Stigma*.—Two parted, 1 mm deep, RHS 66A.

*Stamen*.—4, paired and exerted, top two 8.5 mm long, bottom two are 8 mm long, fused at the base.

*Filament color*.—RHS 48C.

*Anther*.—1 mm long, color closest to RHS 177C.

*Pollen color*.—RHS NN155C.

*Fruit/seed*.—Not observed.

Disease/pest resistance: No unusual resistance or susceptibility noticed to date.

I claim:

1. A new and distinct *Agastache* plant named 'Peach Pearl' substantially as illustrated and described herein.

* * * * *